(12) United States Patent
Berger et al.

(10) Patent No.: US 7,599,892 B1
(45) Date of Patent: Oct. 6, 2009

(54) METHOD FOR SECURE DIAGNOSTIC SCREENING, SERVICING, TREATMENT, AND COMPLIANCE MONITORING FOR SLEEP APNEA IN TRUCK DRIVERS

(75) Inventors: Mark Berger, Houston, TX (US); Helen Francis Berger, Houston, TX (US)

(73) Assignee: MK3SD, Ltd., Houston, TX (US)

( * ) Notice: Subject to any disclaimer, the term of this patent is extended or adjusted under 35 U.S.C. 154(b) by 424 days.

(21) Appl. No.: 11/679,085

(22) Filed: Feb. 26, 2007

(51) Int. Cl.
*G06N 5/00* (2006.01)
(52) U.S. Cl. .............................. 706/3; 706/45
(58) Field of Classification Search ............... 706/3, 706/45, 46
See application file for complete search history.

(56) References Cited

OTHER PUBLICATIONS

Knipling, et al., Individual Differences and the "High-Risk" Commercial Driver, Commercial Truck and Bus Safety Synthesis Program, Transportation Research Board of the National Academies, 2004, pp. 1-51.*
Olson, Assessment of Drowsy-Related Critical Incidents and the 2004 Revised Hours-of-Service Regulations, Master's Thesis, Virginia Polytechnic Institute and State University, 2006, pp. 1-130.*

* cited by examiner

*Primary Examiner*—Wilbert L Starks, Jr.
(74) *Attorney, Agent, or Firm*—Buskop Law Group, PC; Wendy Buskop

(57) ABSTRACT

A secure method for delivering sleep apnea diagnostic services on an at least one commercial driver to a trucking company. The sleep apnea diagnostic services are delivered by a general coordinator using a system. The system includes at least one processor connected to an input device, an output device, and a data storage. The data storage includes a plurality of secure computer instruction. The processor is in encrypted communication with a network which is in encrypted communication with at least one client device.

25 Claims, 12 Drawing Sheets

Health Screening Survey
Step 1 of 3

*Company Information*

Company: [_____100_____]  Driver #: [__102__]

Classification: [__104__]  Location: [____106____]

Date of Hire: [____] ☐ ☐ YES, I am an applicant!
108

*Personal Information*

Last Name: [__110__]  First Name: [__112__]  MI: [114]

DOB: [____116____]  SSN: [_____]
118

Sex: [__]  Height: [____]  Weight: [__] (lbs.)
120       122            124

[Continue to Step 2]

*FIG. 3*

Health screening survey
Step 2 of 3
For each question below, please choose the response that best fits your answer for that Question.

| Health information Question | Answers | |
|---|---|---|
| 1. Do you have high blood pressure? | ⊙ Yes ⊙ No | — 134 |
| 2. Do you have diabetes? | ⊙ Yes ⊙ No | — 136 |
| 3. Have you been treated for heartburn? | ⊙ Yes ⊙ No | — 138 |
| 4. Do you have heart problems? | ⊙ Yes ⊙ No | — 140 |
| 5. Have you ever undergone a heart operation or procedure? | ⊙ Yes ⊙ No | — 142 |
| 6. Do you take any of the following medications: isorbide dinitrate, Isordil, Ismo, nitroglycerin, amiadarone or Cardarone? | ⊙ Yes ⊙ No | — 144 |
| 7. Do you have sleep apnea? | ⊙ Yes ⊙ No | — 146 |
| 8. Do you take any of the following medications: Glucophage, Glucotrol, Actos or Avandia, or any other diabetes medications? | ⊙ Yes ⊙ No | — 148 |
| 9. Do you have COPD (emphysema)? | ⊙ Yes ⊙ No | — 150 |
| 10. Do you have asthma? | ⊙ Yes ⊙ No | — 152 |
| 11. Have you been treated for depression? | ⊙ Yes ⊙ No | — 154 |
| 12. Do you snore louder than talking? | ⊙ Yes ⊙ No | — 156 |
| 13. Does your snoring bother other people? | ⊙ Yes ⊙ No | — 158 |
| 14. Do you take any of the following medications: Plavix, Trental, or Persantine? | ⊙ Yes ⊙ No | — 160 |
| 15. Do you take ANY of the following medications: Protonix, Prevacid, Nexium, Pepcid, or Tagamet? | ⊙ Yes ⊙ No | — 162 |
| 16. On average, do you urinate more than once per night? | ⊙ Yes ⊙ No | — 164 |
| 17. Do you become drowsy while driving? | ⊙ Yes ⊙ No | — 166 |
| 18. Does head, back, neck, or joint pain affect your sleeping? | ⊙ Yes ⊙ No | — 168 |
| 19. Do you take any of the following medications: Vasotec, Cozar, Lotril, Norvasc, Enalapril, Lisinopril, Hydrolchlothiazide, or Lasix? | ⊙ Yes ⊙ No | — 169 |
| 20. Do you take any of the following medications: Inderal, Toprol, Metoprolol, Coreg, or Lopressor? | ⊙ Yes ⊙ No | — 170 |
| 21. Do you take any of the following medications: Digoxin, or Coumadin? | ⊙ Yes ⊙ No | — 172 |
| 22. Do you sleep restlessly or find the blankets on the floor in the morning? | ⊙ Yes ⊙ No | — 174 |
| 23. Has anyone noticed that you quit breathing during your sleep? | ⊙ Yes ⊙ No | — 176 |
| 24. Have you awakened from sleep with gasping breaths? | ⊙ Yes ⊙ No | — 178 |

[Continue to Step 3]

*FIG. 4*

Health Screening Survey
Step 3 of 3
Situational Information
Please indicate your chance of dozing under each of the following scenerios

| Situation | Chance of Dozing | | | |
|---|---|---|---|---|
| 1. Sitting and reading | ⊙ Never | ⊙ Slight | ⊙ Moderate | ⊙ High — 180 |
| 2. Watching TV | ⊙ Never | ⊙ Slight | ⊙ Moderate | ⊙ High — 182 |
| 3. Sitting inactive in a public place (e.g., a theater or meeting) | ⊙ Never | ⊙ Slight | ⊙ Moderate | ⊙ High — 184 |
| 4. As a passenger in a car for an hour without a break | ⊙ Never | ⊙ Slight | ⊙ Moderate | ⊙ High — 186 |
| 5. Lying down to rest anytime circumstances permit | ⊙ Never | ⊙ Slight | ⊙ Moderate | ⊙ High — 188 |
| 6. Sitting and talking to someone | ⊙ Never | ⊙ Slight | ⊙ Moderate | ⊙ High — 190 |
| 7. Sitting quietly after lunch without alcohol | ⊙ Never | ⊙ Slight | ⊙ Moderate | ⊙ High — 192 |
| 8. In a truck or car, while stopping for a few minutes in traffic | ⊙ Never | ⊙ Slight | ⊙ Moderate | ⊙ High — 194 |

For Men Only!
What is your neck size? [   ] — 195

[ Submit Survey ]

*FIG. 5*

Health Screening Survey

Thank you, USER NAME!
We appreciate your taking the time to complete this health screening survey. Your information has been securely processed, and as with all personal medical records, will be kept confidential.

*FIG. 6*

Example Company Health Screening Survey Rankings

You currently have a total of 86 survey respondents, which have been broken down into six categories based on sex, WA (Witnessed Apnea), and EDS (Excessive Daytime Sleepiness).

Respondents ~198  ~199  ~200

| Sex | WA+ | EDS+ / WA- | EDS- / WA- |
|---|---|---|---|
| Male | 26 | 5 | 44 |
| Female | 2 | 1 | 8 |

Find a Survey

SSN: ☐ ☐ ☐  [Find] ~206

Driver #: ☐  [Find] ~208

Last Name: ☐  [Find] ~210

There are currently 14 respondents that have been marked for immediate contact due to self-admitted Sleep Apnea. To view a complete list, click here.

To review survey respondents based on more specific criteria, click here for additional reporting tools.

[Return to Main Menu]

*FIG. 7*

Example Company Survey Respondents: Sleep Apnea Alert!

Download Report

| | Name | SSN | Location | Driver No. | Sex | WA± | Probability | Alert | Date | Date of Hire | Status |
|---|---|---|---|---|---|---|---|---|---|---|---|
| 1. | Berger, Mark B | 123-45-6711 | Location A | 007 | Male | ⊕ | 1.000 | 📜 | 3/27/2006 | 3/27/2005 | |
| 2. | berger, mark b | 222-22-222 | Location B | 123 | Male | ⊕ | 1.000 | 📜 | 2/13/2007 | 2/13/2005 | |
| 3. | Green, Paul | 123-45-6711 | Location B | 00000 | Male | ⊕ | 1.000 | 📜 | 2/15/2006 | 2/15/2005 | |
| 4. | Michael, Johnson | 999-8897766 | Location A | 000066 | Male | ⊙ | 1.000 | 📜 | 11/15/2006 | 11/15/2005 | |
| 5. | Smith, James | 123-45-6776 | Location A | abc123 | Male | ⊕ | 1.000 | 📜 | 11/22/2006 | 11/22/2005 | |
| 6. | Test, Test T. | 111-11-1111 | Location A | 111111 | Male | ⊕ | 1.000 | 📜 | 2/16/2007 | 2/16/2005 | |
| 7. | O'Grady, John | 123-45-6711 | Location B | 00000 | Male | ⊙ | 0.594 | 📜 | 2/15/2006 | 2/15/2005 | ✉ |
| 8. | Gordon, John | | Location A | 00000 | Male | ⊙ | 1.000 | 📜 | 2/15/2006 | 2/15/2005 | |
| 9. | Fills, Christopher | | Location B | 00000 | Male | ⊕ | 0.666 | 📜 | 2/15/2006 | 2/15/2005 | |
| 10. | Turk, Larry | | Location B | 00000 | Male | ⊙ | 0.985 | 📜 | 2/15/2006 | 2/15/2005 | ✉ 📅 ⊚ |
| 11. | Brady, Kim | | Location B | 00000 | Female | ⊙ | 0.000 | 📜 | 2/15/2006 | 2/15/2005 | ✉ 📅 ⊚ |

FIG. 8

Health Screening Survey Results: Berger, Mark B.

*Personal Information*

- 232 — Name: Berger, Mark B.  [Change] —249
- 234 — SSN: 123-45-7-6711
- Company: Example Company  [Change] —249
- Classification: N/A
- 236 — Location: Location A  [Change] —249
- 238 — Driver #: 007  [Change] —249
- Applicant: No  [Change] —249
- 240 — Sex: Male
- Age: 51 yrs. (DOB 4/15/1956)
- Height: 5' 11"
- Weight: 213 (lbs.)

Comments [Edit] —251

[Delete Survey]

*Scoring* —246

Probability Score: 1.000
WA ⊕  EDS ⊕  BMI: 29.7
         245
244

248 — This user has been flagged for a Sleep Apnea Follow-up call!

[Remove Apnea Flag]

*Sleep Test*
This individual has no available test results.

*Follow Up*
There has been no follow-up with this individual.

[Modify]

FIG. 9A

Complete List of Survey Responses (Recorded on 3/27/2006)

Health Information

| | | |
|---|---|---|
| 1. Do you have high blood pressure? | Yes | |
| 2. Do you have diabetes? | Yes | |
| 3. Have you been treated for heartburn? | Yes | |
| 4. Do you have heart problems? | No | |
| 5. Have you ever undergone a heart operation or procedure? | No | |
| 6. Do you take ANY of the following medications: Isordil, Ismo, nitroglycerin, Cardarone, or Amiodarone? | No | |
| 7. Do you have sleep apnea? | Yes | |
| 8. Do you take ANY of the following medications: Glucophage, Glucotrol, Actos, or Avandia, or any other diabetes medications? | Yes | |
| 9. Do you have COPD (emphysema)? | No | |
| 10. Do you have asthma? | No | |
| 11. Have you been treated for depression? | No | |
| 12. Do you snore louder than talking? | Yes | |
| 13. Does your snoring bother other people? | No | |
| 14. Do you take ANY of the following medications: Plavix, Trental, or Persantine? | No | |

Epworth Information

| | |
|---|---|
| 1. Sitting and reading | Never |
| 2. Watching TV | Never |
| 3. Sitting inactive in a public place (e.g., a theater or meeting) | Never |
| 4. As a passenger in a car for an hour without a break | High |
| 5. Lying down to rest anytime circumstances permit | Moderate |
| 6. Sitting and talking to someone | Slight |
| 7. Sitting quietly after lunch without alcohol | Never |
| 8. In a truck or car, while stopping for a few minutes in traffic | Never |

Sex-Specific Information

What is your neck size?

*FIG. 9B*

Complete List of Survey Responses (Recorded on 3/27/2006)
*Health Information*

15. Do you take ANY of the following medications: Protonix, Prevacid, Nexium, Pepcid, or Tagamet?  No
16. On average, do you urinate more than once per night?  No
17. Do you become drowsy while driving?  Sometimes
18. Does head, back, neck, or joint pain affect your sleeping?  Yes
19. Do you take ANY of the following medications: Vasotec, Cozar, Lotril, Norvasc, Enalapril, Lisinopril, Hydrochlorthiazide, or Lasix?  Yes
20. Do you take ANY of the following medications: Inderal, Toprol, Metoprolol, Coreg, Lopressor?  No
21. Do you take ANY of the following medications: Digoxin, Coumadin?  Yes
22. Do you sleep restlessly or find the blankets on the floor in the morning?  Yes
23. Has anyone noticed that you quit breathing during your sleep?  No
24. Have you awakened from sleep with gasping breaths?  Yes

Screening History

| | Date | BMI | WA± | Probability | Alert | Status |
|---|---|---|---|---|---|---|
| 1. | 3/27/2006 | 29.7 | ⊕ | 1.000 | | |

FIG. 9C

Example Company Survey Respondents: Female / EDS- / WA-Filter/Sort Options

Classification: <All Classifications> ▼ — 252

Location: <All Locations> ▼ — 254

Treatment Facility: <All Facilities> ▼ — 256

Sort by: Risk ▼ Desc. ▼  Then by: Date of Entry ▼ Desc. ▼

[Download Report] [Apply Filter]

<Previous   Page 1 of 1

26 Result(s) found

| Name | SSN | Location | Driver No. | Sex | WA± | Probability | Alert | Date | Date of Hire | Status |
|---|---|---|---|---|---|---|---|---|---|---|
| 1. Bama, John | | Location A | 00000 | Male | ⊕ | 1.000 | | 3/27/2006 | 3/27/2005 | |
| 2. Berger, Mark B | 123-45-6711 | Location A | 007 | Male | ⊕ | 1.000 | 🔔 | 3/27/2006 | 3/27/2005 | |
| 3. berger, mark b | 222-22-222 | Location B | 123 | Male | ⊕ | 1.000 | 🔔 | 2/13/2007 | 2/13/2005 | |
| 4. Elk, Christopher | | Location A | 00000 | Male | ⊕ | 1.000 | | 2/15/2006 | 2/15/2005 | |
| 5. Green, Paul | | Location B | 00000 | Male | ⊕ | 1.000 | 🔔 | 11/15/2006 | 11/15/2005 | |
| 6. Lincoln, Larry | 666-55-4444 | Location A | 00000 | Male | ⊕ | 1.000 | | 11/22/2006 | 11/22/2005 | |

METHOD FOR SECURE DIAGNOSTIC SCREENING, SERVICING, TREATMENT, AND COMPLIANCE MONITORING FOR SLEEP APNEA IN TRUCK DRIVERS

FIELD

The present embodiments relate generally to a secure method for providing sleep apnea diagnostic services on at least one commercial driver for at least one trucking company.

BACKGROUND

Sleep apnea is very common, particularly in the commercial driver population. Studies show that up to 28% of commercial drivers may be afflicted. Primary risk factors include being male, overweight, and over the age of forty. Fortunately sleep apnea can be diagnosed and, with treatment, quality of life and health benefits can be realized.

Sleep apnea is defined as the cessation of breathing during sleep. Obstructive sleep apnea (OSA) is the most common form of sleep apnea. OSA occurs when the tissues in the back of the throat repetitively collapse during sleep, producing snoring and complete airway blockage. This blockage creates pauses in breathing that occur repeatedly every night. In severe cases they can occur as frequently as every 30 seconds. Alarmingly, they can last up to a full minute.

These repetitive pauses in breathing during sleep are accompanied by a reduction in blood oxygen levels and are followed by an arousal response. This response includes a release of substances into the bloodstream, which promote elevation of blood pressure, inflammation, insulin resistance, and a disruption of the brain wave sleep pattern. The consequences of untreated sleep apnea include poor quality sleep, excessive daytime fatigue and sleepiness, irritability, hard-to-control high blood pressure and diabetes, heart disease, and stroke. Interestingly and not coincidentally, many of these same medical conditions account for the majority of health-related expenditures in the commercial driver population. Moreover, untreated sleep apnea may be responsible for job impairment and motor vehicle crashes.

Traditional methods for diagnosing sleep apnea in commercial drivers are time consuming and often interfere with the ability to perform their routes, which results in the trucking company as well as the commercial driver suffering economic deprivation.

The recognition of the dangers associated with commercial drivers and improper sleep is evident in the numerous regulations developed to ensure that commercial drivers receive proper sleep. For example, restrictions on the number of hours a commercial driver can drive in a day have been implemented to prevent commercial drivers from driving without proper sleep.

There exists a need to efficiently screen for sleep apnea in commercial drivers.

There exists a need to efficiently determine whether a commercial driver has sleep apnea.

There exists a need to efficiently treat those with sleep apnea.

There exists a need to efficiently monitor a commercial driver's use of sleep apnea treatment equipment.

The present embodiments meet these needs.

BRIEF DESCRIPTION OF THE DRAWINGS

The detailed description will be better understood in conjunction with the accompanying drawings as follows:

FIG. 3 shows an example sleep apnea diagnostic screening questionnaire requesting company personal information and individual personal information usable with the embodiments of this method.

FIG. 4 shows an example sleep apnea diagnostic screening questionnaire requesting health information usable with the embodiments of this method.

FIG. 5 shows an example sleep apnea diagnostic screening questionnaire requesting situational answers from a situational questionnaire usable with the embodiments of this method.

FIG. 6 shows an example of a thank you screen that is shown after completing the health screening survey usable with the embodiments of this method.

FIG. 7 shows an example screen of survey rankings of how a general coordinator would view commercial drivers after they had completed the health screening survey usable with the embodiments of this method.

FIG. 8 shows an example survey rankings usable with the embodiments of this method.

FIG. 9 shows a screen of a commercial driver after an general coordinator had selected them and their answers to the health screening questions usable with the embodiments of this method.

FIG. 10 shows the ability of an general coordinator to filter between different commercial drivers that are in the database usable with the embodiments of this method.

Figure 1:
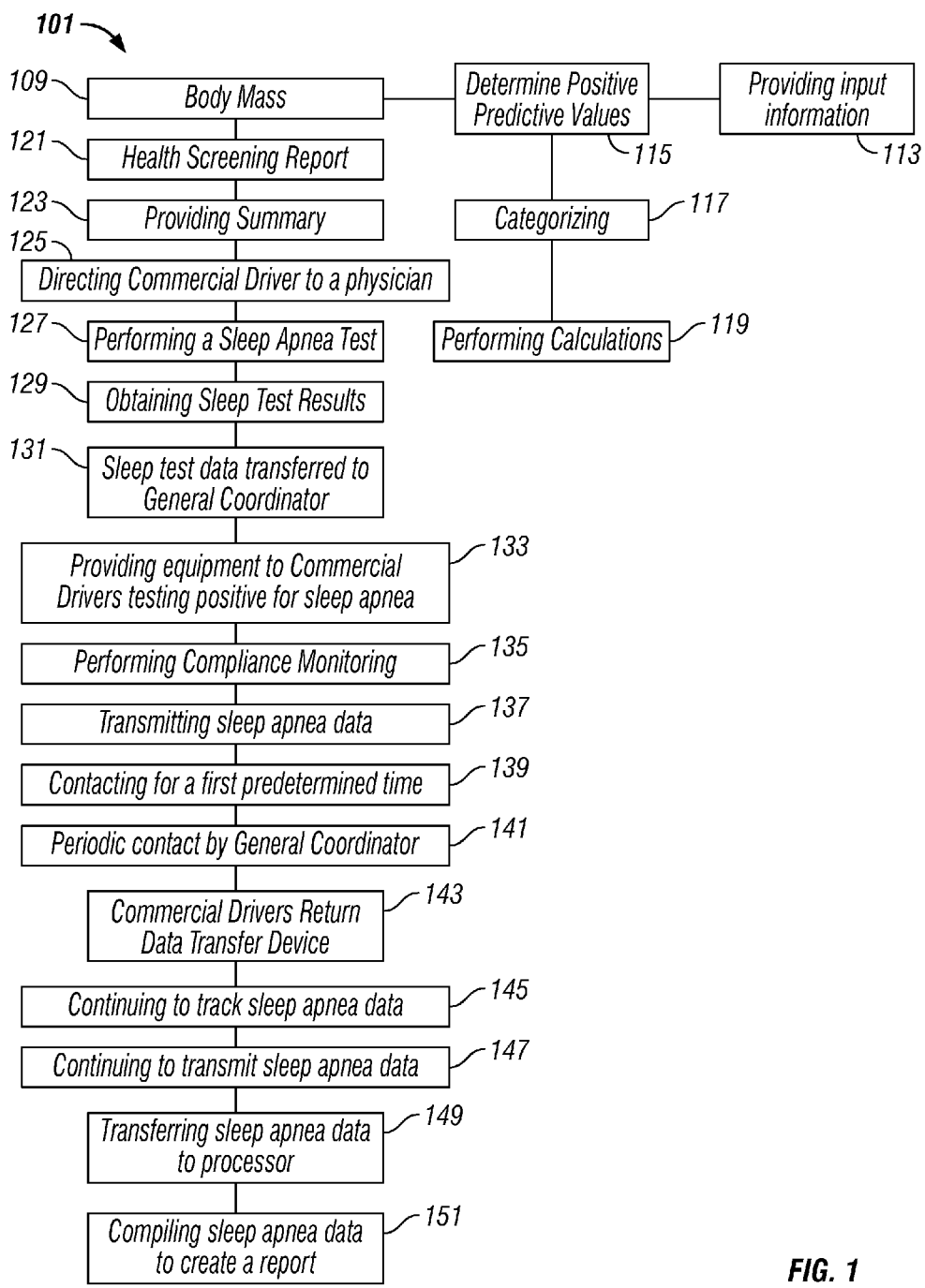
FIG. 1 depicts a general flow diagram of an embodiment of the method.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that they can be practiced or carried out in various ways.

The embodiments of the invention relate generally to a secure method for a general coordinator to deliver sleep apnea screening, sleep apnea treatment, and sleep apnea treatment compliance monitoring on an at least one commercial driver to a trucking company.

The method includes the step of the commercial driver providing input information to the general coordinator. The commercial driver provides input information to the general coordinator by completing a secured sleep apnea diagnostic screening questionnaire.

The secured sleep apnea diagnostic screening questionnaire can request information relating to the trucking company's employee information; the commercial driver's individual personal information, such as his age; the commercial driver's personal health information, such as history of high blood pressure; and similar information pertinent to commercial driver that can be used to screen for sleep apnea.

It is contemplated that the personal information can include information such as the commercial driver's name, an employee number for each commercial driver, such as 12345; gender for each commercial driver; social security number for each commercial driver, such as 123-45-6078; an alert icon for self admitted sleep apnea; date of input of information; date of hire; or at least one trucking company designated field.

Additionally the secured sleep apnea questionnaire can include a situational questionnaire which can include gender related questions, such as neck circumference, or menopausal status.

In an alternative embodiment of the method the input information can be provided to the general coordinator by the commercial driver using a client device to provide answers to the sleep apnea screening questionnaire to the general coordinator.

The client device can be in encrypted communication with a network. The network can be in communication with at least one server. The server can be in communication with an input device, an output device, and a data storage.

The data storage can include encrypted computer instruction for the secure sleep apnea screening questionnaire, and encrypted computer instructions for providing a confirmation e-mail to the commercial driver. The confirmation e-mail can inform the commercial driver of the answers provided to the sleep apnea screening questionnaire, and inform the commercial driver that the information provided in the sleep apnea screening questionnaire is secure and complete.

It is further contemplated that the e-mail can include an interpretation of the sleep apnea screening questionnaire, such as an individualized health screening report. For example the e-mail could inform the commercial driver that he is at high risk for sleep apnea and should be tested for sleep apnea.

The general coordinator determines positive predictive values for sleep apnea by categorizing the input information. The general coordinator can use computer instructions stored on a server to perform the task of categorizing the input information.

The input information can be categorized into the following: male Witnessed Apnea Positive (WA+), female Witnessed Apnea Positive (WA+), male Witnessed Apnea Negative (WA−) and Excessive Daytime Sleepiness Positive (EDS+), female Witnessed Apnea Negative (WA−) and Excessive Daytime Sleepiness Positive (EDS+), male Witnessed Apnea Negative (WA−) and Excessive Daytime Sleepiness Negative (EDS−), or female Witnessed Apnea Negative (WA−) and Excessive Daytime Sleepiness Negative (EDS−).

The input information categorized into male WA− and EDS+, require an odds ratio calculation in combination with a liner regression model to determine the predictive value for sleep apnea for each of the commercial drivers associated with the input information in the groups male WA− and EDS+, female WA− and EDS+.

The input information in the category of male WA− and EDS−, or female WA− and EDS−, and female WA− and EDS+ requires an odds ratio calculation to determine the predictive value of sleep apnea for the commercial drivers associated with the input information associated with the input information categorized into the male WA− and EDS−, female WA− and EDS−, and female WA− and EDS+.

The general coordinator can additionally calculate the body mass index for each of the commercial drivers.

The embodiments of the method can further include the step of the general coordinator providing a health screening service report using the categorized input information to the trucking company. The health screening report is adapted to identify commercial drivers with high predictive values for sleep apnea.

The health screening service report can include a rating of individualized numerical scores indicating a positive predictive value, a high, medium, or low positive predictive value. The positive predictive values can be indicated by a red, yellow, or green flag indicating high, intermediate, or low risk for sleep apnea, respectively. It is contemplated that colors alone can be used without any specific icon to indicate high, medium, or low positive predictive values. It is also contemplated that textual words, high, medium, and low can be used in association with commercial drivers to indicate high, medium, or low positive predictive values.

The health screening service report can include the trucking company's name; the sex of the commercial driver; the presence or absence of sleep apnea; the commercial driver's body mass index, the neck size range of the commercial driver.

It is further contemplated that the health screening service report can include if the commercial driver has self-admitted hypertension; if the commercial driver has self-admitted diabetes; if the commercial driver has self-admitted heart disease; if the commercial driver has self-admitted lung disease; if the commercial has self-admitted asthma; if the commercial driver has self-admitted heart burn; or if the commercial driver has self-admitted frequent urination at night.

Further, the health screening service report can include a look-up table for each commercial driver. The look-up tab can be organized according to the commercial driver's employee number, or social security number.

The commercial drivers with high predictive values for sleep apnea are directed to go to a physician to obtain a prescription for a sleep apnea sleep test. The next step is performing a sleep apnea sleep test on the commercial drivers with the high predictive values for sleep apnea. The sleep apnea sleep test can be used to obtain sleep apnea sleep test data.

The sleep apnea sleep test data is transmitted to the general coordinator. The sleep apnea sleep test data is analyzed to determine which of the commercial drivers have sleep apnea. The transmission from the physician can be by e-mail, fax, post, or courier.

The general coordinator can provide sleep apnea treatment equipment to the commercial drivers with sleep apnea simultaneously with the conclusion of the sleep apnea sleep test.

Providing the sleep apnea treatment equipment to the commercial drivers simultaneously with the conclusion of the sleep apnea sleep test is an improvement over traditional methods for treating sleep apnea. With traditional methods for treating sleep apnea it can take several days or weeks for the commercial driver to receive treatment equipment.

The delay in the commercial driver receiving the sleep apnea treatment equipment can delay the commercial driver's deliveries. The delay in the commercial driver's deliveries is a great cost to the commercial driver and to the trucking company.

The cost associated with the delays in the commercial driver's deliveries has traditionally prevented trucking companies from seeking sleep apnea treatment for commercial drivers. By simultaneously providing the sleep apnea treatment equipment to the commercial drivers with sleep apnea at the conclusion of the sleep apnea sleep test the delay in the commercial driver's deliveries is eliminated.

The sleep apnea treatment continuous positive airway pressure (CPAP) machine has a compliance chip for monitoring the usage and efficacy of the sleep apnea treatment equipment. A data transfer device can be paired with the CPAP machine.

The method further includes the step of the general coordinator performing compliance monitoring on the commercial drivers that tested positive for sleep apnea. The commercial drivers with sleep apnea use the data transfer device to transmit sleep apnea treatment equipment data from the sleep apnea treatment equipment, such as the CPAP machine, to the general coordinator. The sleep apnea treatment equipment data can include data, such as mask leakage, hours of use, and an apnea index based on throat closure during CPAP machine treatment.

The data transfer device is adapted for use with a data transfer system, such as a beeper data transfer system, a cell phone data transfer system, a hardwired system, or a wireless data transfer system. The data transfer system is adapted to transmit sleep apnea treatment equipment data from the data transfer device to the general coordinator.

The present embodiment of the method further includes the step of the general coordinator contacting each commercial driver with sleep apnea after a first predetermined period of continuous compliance monitoring. During the contacting the general coordinator ascertains sleep apnea treatment equipment performance. The general coordinator at this time can conduct trouble shooting to make sure that there is optimal performance of the CPAP machine, and the other sleep apnea treatment equipment. The first predetermined time of compliance monitoring can be for a range between 2 days and 3 days.

For example the general coordinator can ask the commercial driver if the mask is fitting fine and/or if the mask is leaking. If the commercial driver indicates that the mask is leaking the general coordinator can recommended various actions that can remedy the leaking mask, such as tightening the mask, loosening the mask, adjusting the position of the mask and/or connecting hose, or suggesting a different type of mask.

The general coordinator contacts each commercial driver periodically following the first predetermined period of continuous compliance monitoring. The general coordinator periodically contacts the commercial drivers with sleep apnea to ascertain sleep apnea treatment equipment performance, and to help trouble shoot any problems the individual commercial drivers with sleep apnea may be experiencing.

During the periodic contacting of the commercial drivers with sleep apnea the general coordinator can contact the commercial drivers with sleep apnea weekly. It is contemplated that during the periodic contacting of the commercial drivers with sleep apnea the commercial drivers will contact the general coordinator. In the alternative the general coordinator can initiate the communication with the commercial drivers with sleep apnea during the periodic contacting. The periodic contacting is continued for a second predetermined time.

After the second predetermined time the individual commercial drivers with sleep apnea each return the data transfer devices to the general coordinator. The second predetermined time of continuous compliance monitoring can be for a period of time ranging between 2 weeks and 4 week It is contemplated that the general coordinator can continue to track sleep apnea treatment equipment data for each commercial driver, by using the compliance chip installed in the CPAP machine. The general coordinator would comply with specified requirements established by the trucking company, and/or the US Department of Transportation (DOT).

The next step in this embodiment of the method includes the general coordinator continuing to track sleep apnea treatment equipment data for each of the commercial drivers with sleep apnea.

Then each commercial driver with sleep apnea downloads the sleep apnea treatment equipment data to an encrypted removable data storage device.

After the commercial drivers with sleep apnea download the sleep apnea treatment equipment data the general coordinator transfers the sleep apnea treatment equipment data from the encrypted removable data storage device to a processor. The transferred sleep apnea treatment equipment data from the encrypted removable data storage device to processor comprises between 2 months to 4 months of sleep apnea treatment equipment data.

It is contemplated that the encrypted removable data storage device can be flash memory cards, flash drives, portable hard drives, memory cards, modems, and direct cable connections to the processor, such as a data card from ResMed™ or a removable data storage device from Respironics™.

The general coordinator can compile the sleep apnea treatment equipment data using the processor. Additionally, the general coordinator can generate a sleep apnea treatment compliance status report. The general coordinator can provide the compliance status report for each of the commercial drivers to the appropriate trucking companies.

It is further contemplated that an embodiment of the method can include delivering sleep apnea screening, sleep apnea treatment, and sleep apnea treatment compliance monitoring simultaneously on a plurality of commercial drivers simultaneously to a plurality of trucking companies.

The method can further include providing separate commercial drivers results to the trucking companies employing each of the commercial drivers simultaneously.

The present method can screen for sleep apnea, treat sleep apnea, and perform compliance monitoring, thus contributing to a reduced risk for potentially dangerous vehicular accidents, thereby preventing costly loss or damage of equipment, loss of time, preventing injury, and saving lives. Treated sleep apnea has also been shown to improve ones health through better control of blood pressure and diabetes, and a reduced risk for heart attacks and stroke.

It is contemplated that the method can also include creating additional reports. The additional reports can be reports on the sleep test data, can be a report on receipts verifying delivery of equipment.

An alternative embodiment of the method can further include the step of confirming the trucking company has a United States Health Insurance Portability and Accountability Act (HIPAA) of 2002, 42 C.F.R. §164, pages 685-740 compliant release for each commercial driver. It is contemplated that the present method can be compliant under the United States Health Insurance Portability and Accountability Act (HIPAA) of 1996, the final regulation of the HIPAA privacy rule of December 2000, and the Final Rule modifications of August 2002. It is further contemplated that any protected health information (PHI) obtained using the present method can be de-identified when stored and processed to further comply with the requirements of HIPAA.

FIG. 1 is a flow diagram for an embodiment of the method for delivering sleep apnea screening, sleep apnea treatment, and sleep apnea treatment compliance monitoring on an at least one commercial driver to a trucking company by a general coordinator 101. The trucking company can be a commercial trucking company, an interstate trucking company, or a intrastate trucking company.

The general coordinator can be a doctor, health clinic, healthcare network, or a provider of sleep apnea-related services who coordinates with the physician and a third party vendor, such as a manufacturer of CPAP machine and related equipment supplying sleep apnea treatment equipment.

The first step in the method involves the commercial driver providing input information to the general coordinator using a sleep apnea diagnostic screening questionnaire 113. For example, the commercial driver can go to the trucking company's office and complete the sleep apnea diagnostic screening questionnaire by hand.

Figure 2:
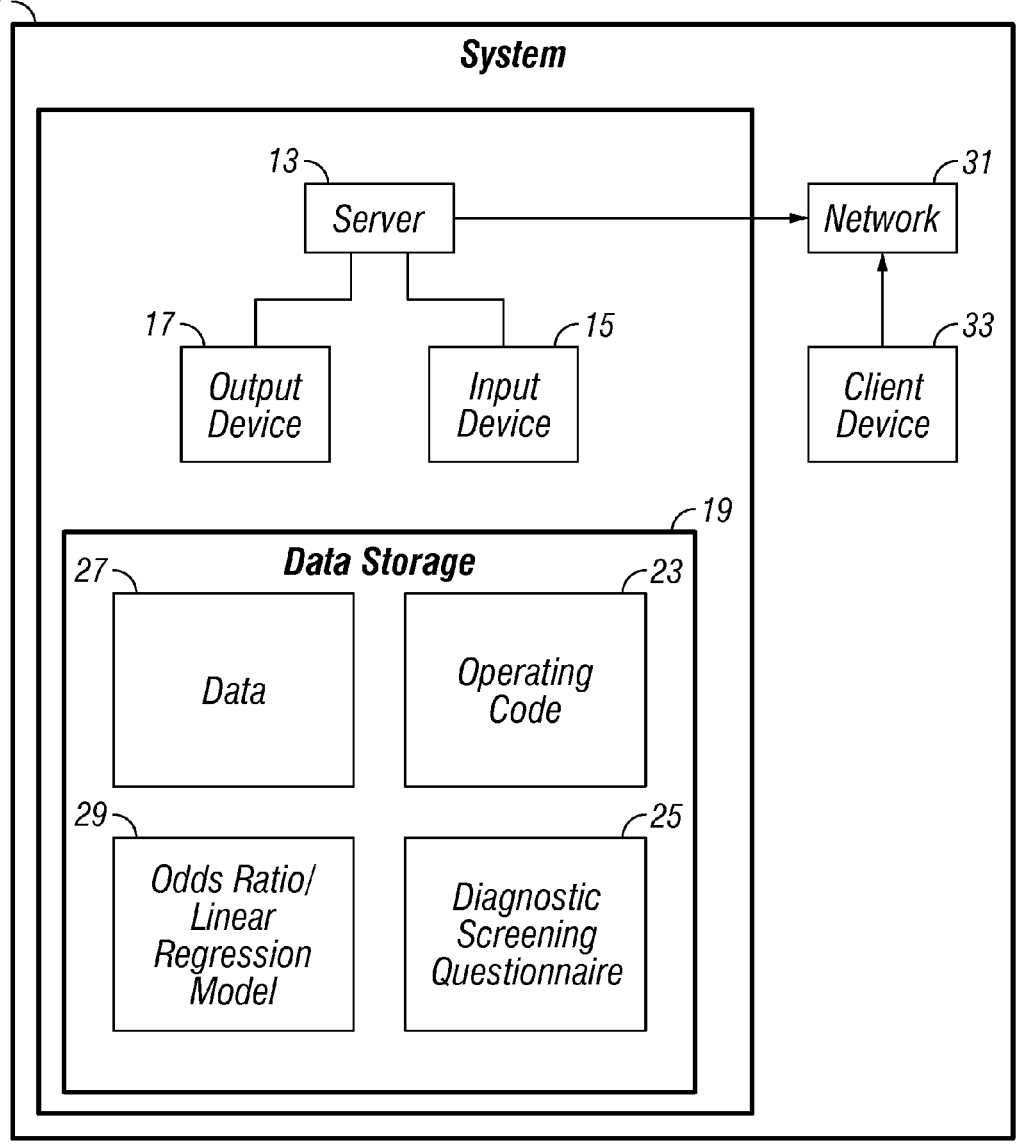
FIG. 2 depicts a system usable with the embodiments of the method.

Alternatively, the general coordinator can use a system such as the one depicted in FIG. 2, which would allow the commercial driver to electronically fill out the sleep apnea diagnostic screening questionnaire using a network, such as the internet, a WAN line, a local area network, and similar communication networks. The network is in communication with a client device, such as a personal computer.

After the sleep apnea diagnostic screening questionnaire is completed the general coordinator determines positive predictive values for sleep apnea of each of the at least one commercial drivers and generates a probability 115 by categorizing the input information 117 and performing associated calculations 119. The input information is categorized using secured input instructions on a server.

The input information can be categorized into the following: male Witnessed Apnea Positive (WA+), female Witnessed Apnea Positive (WA+), male Witnessed Apnea Negative (WA−) and Excessive Daytime Sleepiness Positive (EDS+), female Witnessed Apnea Negative (WA−) and Excessive Daytime Sleepiness Positive (EDS+), male Witnessed Apnea Negative (WA−) and Excessive Daytime Sleepiness Negative (EDS−), or female Witnessed Apnea Negative (WA−) and Excessive Daytime Sleepiness Negative (EDS−).

The input information categorized into male WA− and EDS+, require an odds ratio calculation in combination with a liner regression model to determine the positive predictive value for sleep apnea for each of the commercial drivers associated with the input information in the groups male WA− and EDS+.

The input information in the category of male WA− and EDS−, female WA− and EDS−, and female WA− and EDS+ requires an odds ratio calculation to determine the positive predictive value of sleep apnea for the commercial drivers associated with the input information associated with the input information categorized into the male WA− and EDS−, female WA− and EDS, and female WA− and EDS+.

The general coordinator can also make a calculation of the body mass index for each of the at least one commercial drivers 109, this is usually done simultaneously when the general coordinator determines the commercial drivers probability for sleep apnea 115.

The next step is providing a health screening service report 121. The general coordinator provides the health screening service report to the trucking company. The health screening service report is adapted to identify commercial drivers with high predictive values for sleep apnea. In this embodiment of the method the general coordinator also provides a summary of all positive predictive values using input information to the trucking company 123, such as a listing of the probabilities of sleep apnea.

For example the health screening service report can indicate that a commercial driver has inputted data into the sleep apnea diagnostic screening questionnaire that indicates a high likelihood of sleep apnea and recommend that the commercial driver receive a sleep apnea sleep test. In the alternative the health screening report could indicate that the data inputted into the sleep apnea diagnostic screening questionnaire indicates that the commercial driver has a low predictive value for sleep apnea and that he does not need to receive a sleep apnea sleep test.

In this embodiment the next step is directing the commercial drivers with high predictive values for sleep apnea to go to a physician to obtain a prescription for a sleep apnea sleep test 125. Once the commercial drivers with sleep apnea receive the prescription for the sleep apnea sleep test the next step is performing a sleep apnea sleep test on the commercial drivers with a high positive predictive value for sleep apnea 127, such as an 80 to 90 percent positive predictive value.

The sleep apnea sleep test can be performed for one night to obtain sleep apnea sleep test data 129, such as amount of time asleep, EEG stages of sleep, number of respiratory events while asleep, blood oxygen levels while asleep, and leg movements present while asleep.

The next step in this embodiment of the method can be the physician transmitting the sleep apnea sleep test data to the general coordinator 131. The transmission of the sleep test data can be by electronic transfer, written transmission, or verbal transmission by using traditional means of communication, such as fax, e-mail, or a telephone. The sleep apnea sleep test can be conducted at a free-standing sleep diagnostic facility, a hospital-based sleep diagnostic facility, or an unattended home sleep diagnostic protocol.

After the sleep apnea sleep test, the next step in this embodiment of the method is the general coordinator providing sleep apnea treatment equipment to the commercial drivers testing positive for sleep apnea 133. The sleep apnea treatment equipment has a data transfer device paired with the CPAP machine and related equipment such as masks. The CPAP machine has a compliance chip resident in the CPAP machine to monitor hours of usage, mask leakage, and apnea index. The sleep apnea treatment equipment is supplied simultaneously with the conclusion of the sleep apnea sleep test.

Subsequent to providing sleep apnea treatment equipment to the commercial drivers having sleep apnea the next step of this embodiment of the method is the general coordinator performing compliance monitoring on the commercial drivers that have sleep apnea 135. A receipt can be scanned and uploaded into the files of the commercial truck driver and provided to the truck company for the equipment provided to the commercial driver.

The next step in this embodiment of the method involves the commercial driver transmitting sleep apnea treatment equipment data, such as the CPAP machine's performance and hours of use, from the sleep apnea treatment equipment to the general coordinator 137. The commercial drivers initially utilize wireless transmission technology to transmit sleep apnea treatment equipment data to the general coordinator. The wireless transmission of data from the compliance chip to the coordinator can utilize a beeper data transfer system, a cell phone data transfer system, or a satellite wireless data transfer system.

The method further involves the general coordinator contacting each commercial driver with sleep apnea for a first predetermined period of continuous compliance monitoring 139, such as within the first 72 hours of treatment initiation, to additionally evaluate sleep apnea treatment equipment performance and driver CPAP machine comfort and compliance. Sleep apnea treatment equipment performance can include number of hours and days of usage of the CPAP machine, mask leak quantification, and apnea index, which is the number of times the commercial driver's throat closes off during CPAP machine treatment.

Following the first predetermined period the general coordinator periodically contacts each commercial driver. For example the general coordinator can periodically contact the commercial drivers with sleep apnea for about two to about eight weeks by phone to ascertain sleep apnea treatment equipment performance and the commercial driver's CPAP machine comfort and compliance. The periodic contacting could be the general coordinator or a designate of the general coordinator contacting the commercial drivers with sleep apnea once a week. The periodic contacting can take place during a second predetermined time of continuous compliance monitoring.

After the second predetermined time of continuous compliance monitoring, such as about 15 to about 60 days, each of the commercial drivers with sleep apnea perform the step of returning the data transfer device to the general coordinator 143.

The next step in this embodiment of the method is that the general coordinator or a designate of the general coordinator continuing to track sleep apnea treatment equipment data for each of the commercial drivers with sleep apnea 145. The general coordinator or designate can continue to track sleep apnea treatment equipment data for each of the commercial drivers with sleep apnea by requesting the driver to download the CPAP machine's compliance chip data onto a portable memory card.

The commercial drivers with sleep apnea perform the step of downloading sleep apnea treatment equipment data to an encrypted removable data storage device 147. The encrypted removable data storage device can be a data card or other flash memory device.

Next the general coordinator or a designee of the general coordinator performs the step of transferring sleep apnea treatment equipment data from the encrypted removable data storage device to a processor 149. The processor can be a personal computer, a wearable computer, a hand-held computer, a lap top computer, or a similar device, such as a cellular telephone with advanced memory capability.

The general coordinator can perform the step of compiling the sleep apnea treatment equipment data using the processor to create a compliance report 151. The compliance report can include information such as average number of hours per night the driver used his CPAP machine.

FIG. 2 is an embodiment of the system 11 that can be used with embodiments of the method for at least one commercial driver to input data into a sleep apnea screening questionnaire. The system 11 includes a server 13, such as a processor associated with data storage having an input device and an output device with the computer instructions resident in the data storage. The server 13 is depicted connected to an input device 15, which can be a keyboard, a tactile display screen, an audio input device with voice recognition software, a cellular device, or similar devices.

The server 13 is also connected to an output device 17, such as a microphone using text to speech software, a digital monitor, a cellular telephone, a printer, a computer, or combinations thereof.

The server 13 is connected to a data storage 19, such as a memory card, a flash drive, or a similar memory device. The data storage 19 contains a plurality of secure computer instructions. For example, the data storage has operating code 23, computer instruction for the sleep apnea diagnostic screening questionnaire 25, computer instructions for performing an odds ratio and/or a linear regression model 29, and computer instructions for compiling data 27.

The server 13 is in encrypted communication with a network 31, such as the internet, a local area network, a wide area network, a virtual private network, a cellular network, a fiber optic network, or other similar networks. The network 31 is in encrypted communication with at least one client device 33, such as a personal computer.

In an embodiment the computer instructions can further include a dataset using outcomes from at least 500 commercial drivers. The dataset can be used to form a useable linear regression model for determining positive predictive values for sleep apnea.

For example an odds ratio model can be first utilized in determining risk stratification for sleep apnea in all groups. Individual odds ratios can be assigned to specific health conditions and specific symptoms based on results from published medical research. These odds ratios can be modified based on outcome data available on 115 commercial drivers tested for sleep apnea. A composite odds ratio value can be calculated as the product of all individual odds ratios.

Retrospective analysis of 115 commercial drivers tested for sleep apnea demonstrated that a composite odds ratio of 8.0 or greater for male, and 1.9 or greater for female, Witnessed Apnea Negative (WA−) and Excessive Daytime Sleepiness Negative (EDS−) would generate a high positive predictive value of at least 85%.

A subsequent analysis of over 500 additional commercial drivers tested for sleep apnea confirmed an 88% positive predictive value for these groups from the odds ratio model.

A retrospective analysis of 115 commercial drivers tested for sleep apnea demonstrated that the presence of witnessed apnea (WA+) was highly predictive for sleep apnea. For this reason, all commercial drivers reporting witnessed apnea were considered at high risk for sleep apnea. A subsequent analysis of over an additional 500 commercial drivers tested for sleep apnea confirmed a 90% positive predictive value for this single risk factor.

Subsequent analysis of over an additional 500 commercial drivers confirmed the aforementioned statistical model capable of a greater than 85% positive predictive value for sleep apnea in all groups except for male Excessive Daytime Sleepiness Positive (+), Witnessed Apnea (−). For this group it was necessary to apply a linear regression following a composite odds ratio calculation.

To generate the linear regression model for all male users indicating a positive response for excessive daytime sleepiness EDS (+), witnessed apnea negative WA (−), a model was created by exploring all possible models with main effects and pair-wise interactions with the following variables: body mass index, age, hypertension, diabetes, heartburn, heart condition, snoring, asthma, depression, frequent urination at night, and painful sleep.

The "best" model was chosen by using both forward and backward selection using the aic criterion (the function step in R). After selecting this model, subjects were assigned a probability of apnea (inverse log odds of linear combination). Using the usual 0.5 cutoff on the estimated probability, a cross-validated positive-predictive value of 0.876 was achieved. To get to the goal of 0.88, a cutoff of 0.65 was preferred. This gave an estimated 0.891 positive predictive value using cross-validation.

FIG. 3 shows an example health screening survey requesting company personal information and individual personal information. Company information that a user may input include name of Company (100), such as Precision Pulmonary Diagnostics, Driver number (102), such as 12468, Classification (104), such as dedicated driver, location (106), such as Houston Operating Center, and date of hire (108), such as Feb. 13, 2007. Other information that is not depicted but can be entered can include a box for indicating whether a driver is experienced. Personal information that a user may input include last name (110), first name (112), middle initial (114), date of birth (116), social security number (118), sex (120), height (122), and weight (124). Other information that is not depicted but can be entered can include an indication of a user's smoking history, or a history of nasal or sinus conditions, or indications of other health conditions, such as hypertension or diabetes.

FIG. 4 depicts an example sleep apnea diagnostic questionnaire requesting health information such as health conditions, personal symptoms, prior operations, and medications. Some of these questions can include: Do you have high blood pressure? (134), Do you have diabetes? (136), Have you been treated for heartburn? (138), Do you have heart problems? (140), Have you ever undergone a heart operation or procedure? (142), Do you take any of the following medications: isorbide dinitrate, such as Isordil™ or Ismo™, nitroglycerin, amiodarone, such as Cardarone™? (144), Do you have sleep apnea? (146), Do you take ANY of the following medications: metformin, such as Glucophage™, glyburide, such as Glucotrol™, Actos™, or Avandia™, or any other diabetes medications? (148), Do you have COPD (emphysema)? (150), Do you have asthma? (152), Have you been treated for depression? (154), Do you snore louder than talking? (156), Does your snoring bother other people? (158), Do you take ANY of the following medications: Plavix™, Trental™, or Persantine™? (160), Do you take ANY of the following medications: Protonix™, Prevacid™, Nexium™, Pepcid™, or Tagamet™? (162), On average, do you urinate more than once per night? (164), Do you become drowsy while driving? (166), Does head, back, neck, or joint pain affect your sleeping? (168), Do you take ANY of the following medications: enalapril, such as Vasotec™, Cozar™, Lotril™, Norvasc™, lisinopril, hydrochlorthiazide, or furosemide, such as Lasix™? (169), Do you take ANY of the following medications: Inderal™, Toprol™, Metoprolol™, Coreg™, or Lopressor™? (170), Do you take ANY of the following medications: Digoxin™, Coumadin™? (172), Do you sleep restlessly or find the blankets on the floor in the morning? (174), Has anyone noticed that you quit breathing during your sleep? (176), and Have you awakened from sleep with gasping breaths? (178). Other information that is not depicted but can be entered can include an indication of a commercial driver's smoking history, or a history of nasal or sinus conditions, or indications of other health conditions.

FIG. 5 shows an example health screening survey requesting situational answers from a situational questionnaire. The questions ask an user to input their chance of dozing while performing certain tasks. Typical tasks that are asked include: Sitting and reading (180), Watching TV (182), Sitting inactive in a public place (184), As a passenger in a car for an hour without a break (186), Lying down to rest anytime circumstances permit (188), Sitting and talking to someone (190), Sitting quietly after lunch without alcohol (192), and In a truck or car, while stopping for a few minutes in traffic (194). Figure four can also include a question requesting a male user to input his neck size (195).

FIG. 6 shows an example of a thank you screen that is shown after completing the health screening survey (196). A user would not be sent to this screen if any of the previous questions asked by the web based questionnaire was not answered. In a contemplated embodiment, the screen depicted in FIG. 5 can also include an electronic copy of a user's responses to the web based questionnaire for the user's records. It is also contemplated that an acknowledgement or verification, such as an e-mail, could also be sent and could include this information.

FIG. 7 shows an example screen of survey rankings of how an administrator would view users after they had completed the sleep apnea diagnostic screening questionnaire. Respondents are split between male and female respondents. In addition, respondents are separated into three different categories based upon the presence or absence of witnessed apneas and the presence or absence of excessive daytime sleepiness determined by each user's input information and questionnaire responses. The three categories are witnessed apnea positive (WA+) (198), witnessed apnea negative (199) and excessive daytime sleepiness positive (WA–/EDS+), and witnessed apnea negative and excessive daytime sleepiness negative (WA–/EDS–) (200). The witnessed apnea positive (198), the witnessed apnea negative and excessive daytime sleepiness positive (199), and witnessed apnea negative and excessive daytime sleepiness negative (200) categories list the number of male and female users which relate to each category. Individual users can be located as well by their social security number (206), driver number (208), and last name (210).

FIG. 8 shows an example survey rankings of how a general coordinator would be able to select commercial drivers and view their status of whether or not they had been contacted and other pertinent information. Commercial drivers would be listed with information showing their name (212), social security number (214), location (216), driver number (218), sex (220), presence or absence of witnessed apnea (225), risk rating for sleep apnea (224), whether or not they have responded positively to a question asking whether they have sleep apnea, notated as alert (226), date of entry (228), date of hire (229), and status of contacting, scheduling, and testing the commercial driver (230). The status of contacting the commercial driver (230) can include an indication that the commercial driver has been referred (231), an indication that the commercial driver has been contacted (233), an indication that the commercial driver has been scheduled for a sleep study (235), and an indication that the commercial driver has completed a sleep study (237). Additional ways that commercial drivers can be listed can include additional fields and columns tailored to the needs of a client.

FIG. 9 shows a screen of an user after an administrator had selected them and their answers to the health screening questions. Individual information of the user is shown including their name (232), social security number (234), location (236), driver number (238), sex (240), presence or absence of witnessed apnea (244), presence or absence of excessive daytime sleepiness (245), probability (246), whether or not they have been flagged for a sleep apnea follow-up (248) and a complete list of their survey responses is shown (250). FIG. 8 also includes change buttons (249), which allow a client or administrator to change or correct personal and company information, such as when a user makes a typographical error. FIG. 8 also includes a comment section (251), which allows one or more clients or administrators to enter comments regarding a specific user or specific user information, such as how a user was referred, pertinent information regarding a user's medical history, and other information. FIG. 8 is also depicted having a screening history (253) for the user. Additional individual information of the user that can be shown include an indication of smoking history, a history of nasal or sinus conditions, or other health information or information regarding medical conditions or medical history.

FIG. 10 shows the abilities of an administrator to sort and filter different users that are in the database. Different filters that an administrator can utilize include classifications (252), locations (254), and treatment facilities (256), which can be any testing facility where a sleep test is performed. An administrator can also use one or more sort menus (258), and sort by categories such as probability and status. Additional filters or sort menus that can be used include a filter or sort menu relating to administrative status, a filter relating to whether a driver is experienced, or a filter relating to date of entry or date of hire.

While these embodiments have been described with emphasis on the embodiments, it should be understood that within the scope of the appended claims, the embodiments might be practiced other than as specifically described herein.

What is claimed is:

1. A method for delivering sleep apnea screening, sleep apnea treatment, and sleep apnea treatment compliance monitoring on an at least one commercial driver to a trucking company by a general coordinator comprising:

the sleep apnea screening comprising:
   a. providing input information to the general coordinator using a secured sleep apnea diagnostic screening questionnaire completed by the at least one commercial driver;
   b. determining positive predictive values for sleep apnea by categorizing input information using computer instructions on a server to categorize the input information into a member of the group consisting of: male Witnessed Apnea Positive (WA+), female Witnessed Apnea Positive (WA+), male Witnessed Apnea Negative (WA−) and Excessive Daytime Sleepiness Positive (EDS+) requiring an odds ratio calculation, female Witnessed Apnea Negative (WA−) and Excessive Daytime Sleepiness Positive (EDS+) requiring an odds ratio calculation, male Witnessed Apnea Negative (WA−) and Excessive Daytime Sleepiness Negative (EDS−) requiring an odds ratio calculation, or female Witnessed Apnea Negative (WA−) and Excessive Daytime Sleepiness Negative (EDS−) requiring an odds ratio calculation;
   c. providing a health screening service report using the categorized input information from the general coordinator to the trucking company adapted to identify commercial drivers with high predictive values for sleep apnea
   d. providing a summary of all positive predictive values using input information to the trucking company; and the sleep apnea treatment comprising:
   e. directing at least one commercial driver to a physician to prescribe a sleep test for sleep apnea and transmitting the results of the sleep test to the general coordinator;
   f. providing sleep apnea treatment equipment comprising a data transfer device paired with a CPAP machine comprising a compliance chip by the general coordinator to the at least one commercial driver indicated by the sleep apnea test data to have sleep apnea simultaneously when the sleep apnea sleep test concludes;

the sleep apnea treatment compliance monitoring comprising:
   g. using the data transfer device by the at least one commercial driver to transmit sleep apnea treatment equipment data from the sleep apnea treatment equipment to the general coordinator;
   h. contacting each at least one commercial driver with sleep apnea by the general coordinator after a first predetermined period of continuous compliance monitoring to ascertain sleep apnea treatment equipment performance; and
   i. following the first predetermined period contacting each at least one commercial driver with sleep apnea periodically by the general coordinator to ascertain sleep apnea treatment equipment performance.

2. The method of claim 1, wherein after the first predetermined period further comprising the step of:
   a. returning the data transfer device by each of the at least one commercial drivers with sleep apnea to the general coordinator after a second predetermined period of continuous compliance monitoring;
   b. continuing to track sleep apnea treatment equipment data for each of the at least one commercial drivers with sleep apnea by the general coordinator;
   c. downloading sleep apnea treatment equipment data by each commercial driver with sleep apnea to an encrypted removable data storage device;
   d. transferring sleep apnea treatment equipment data from the encrypted removable data storage device to a processor by the general coordinator; and
   e. compiling the sleep apnea treatment equipment data using the processor to create a compliance report.

3. The method of claim 2, wherein the data transfer device is adapted for use with a data transfer system.

4. The method of claim 3, further comprising transmitting sleep apnea treatment equipment data from the sleep apnea treatment equipment to the general coordinator using the data transfer system.

5. The method of claim 2, further comprising continuing to track sleep apnea treatment equipment data for each commercial driver while complying with specified requirements established by the trucking company after the second predetermined time of continuous compliance monitoring by the general coordinator.

6. The method of claim 5, wherein the second predetermined time of continuous compliance monitoring comprises a range between 2 weeks and 4 weeks.

7. The method of claim 2, wherein the encrypted removable data storage device comprises flash memory cards, flash drives, portable hard drives, memory cards, modems, and direct cable connections to the processor.

8. The method of claim 2, further comprising providing the compliance report for the at least one commercial driver with sleep apnea to the trucking company by the general coordinator.

9. The method of claim 2, further comprising associating the compliance report and the health screening service report by the general coordinator with each of the at least one commercial driver.

10. The method of claim 1, wherein the input information to the general coordinator further comprises providing answers to the secure sleep apnea screening questionnaire to the general coordinator by the at least one commercial driver using a client device connected in encrypted communication with a network further in communication with at least one server; and wherein the at least one server communicates with an input device, an output device, and a data storage, wherein the data storage comprises encrypted computer instructions for the sleep apnea screening questionnaire, and encrypted computer instructions providing a confirmation e-mail to the at least one commercial driver by the server.

11. The method of claim 1, wherein the sleep apnea treatment equipment data provides hours of use, data on mask leakage, and an apnea index based on throat closure during sleep apnea treatment compliance monitoring.

12. The method of claim 1, further comprising providing delivery of sleep apnea screening, sleep apnea treatment, and sleep apnea treatment compliance monitoring simultaneously on a plurality of commercial drivers and simultaneously to a plurality of trucking companies.

13. The method of claim 1, wherein the method is compliant with the United States Health Insurance Portability and Accountability Act of 2002, 42 C.F.R. section 164, pages 685-740.

14. The method of claim 1, further comprising providing an individualized health screening service report to the at least one commercial driver.

15. The method of claim 1, further comprising providing the individualized health screening service report by e-mail.

16. The method of claim 1, wherein the individual personal information comprises:
   a. name of user;
   b. an employee number for each user;
   c. gender for each user;
   d. social security number for each user;
   e. an alert icon for self admitted sleep apnea;
   f. date of input of information;
   g. date of hire; or
   h. at least one client designated field.

17. The method of claim 1, further comprising compiling the results of the sleep apnea sleep test with the categorized input information to provide a summary of data of the sleep apnea sleep test administered to at least one commercial driver of the commercial trucking company with the categorized input information.

18. The method of claim 1, capable of generating a health screening survey report for the client comprising a member of the group comprising of:
   a. client name;
   b. sex of user;
   c. presence of absence of sleep apnea;
   d. body mass index;
   e. hypertension;
   f. diabetes;
   g. heart disease;
   h. neck size range;
   i. lung disease;
   j. asthma;
   k. heart burn;
   l. frequency urination at night; and
   m. combinations thereof.

19. The method of claim 1, further comprising flagging at least one user with self admitted sleep apnea for additional validation data supporting self admitted sleep apnea.

20. The method of claim 1, wherein the health screening service report comprises a look-up table for each at least one user by name, employee number, or social security number.

21. The method of claim 1, further comprising creating additional reports comprising:
   a. sleep test results;
   b. compliance reports; or
   c. receipts verifying delivery of equipment.

22. The method of claim 1, further comprising confirming the client has a United States Health Insurance Portability and Accountability Act of 2002 42 CFR section 164, pages 685-740 compliant release for each of the at least one commercial drivers.

23. The method of claim 1, wherein the sleep apnea screening questionnaire comprises, wherein the secured sleep apnea diagnostic screening questionnaire comprises:
   a. company employee information;
   b. individual personal information;
   c. personal health information.

24. The method of claim 1, wherein the sleep apnea screening further comprises completing a situational questionnaire comprising gender related questions.

25. The method of claim 1, wherein the health screening service report comprises:
   a. at least one rating per at least one commercial driver, wherein the rating comprises an member of the group consisting of:
   b. individualized numerical scores indicating a positive predictive value for at least one commercial driver;
   c. a high, medium, or low positive predictive value for at least one commercial driver; or combinations thereof.

* * * * *